(12) United States Patent  
Mattila et al.

(10) Patent No.: US 9,990,469 B2
(45) Date of Patent: *Jun. 5, 2018

(54) INFERRING A STATE OF A SYSTEM OVER TIME

(71) Applicant: Combinostics Oy, Tampere (FI)

(72) Inventors: Jussi Mattila, Tampere (FI); Jyrki Lotjonen, Tampere (FI); Juha Koikkalainen, Tampere (FI)

(73) Assignee: COMBINOSTICS OY, Tampere (FI)

( * ) Notice: Subject to any disclaimer, the term of this patent is extended or adjusted under 35 U.S.C. 154(b) by 824 days.

This patent is subject to a terminal disclaimer.

(21) Appl. No.: 14/378,847

(22) PCT Filed: Feb. 13, 2013

(86) PCT No.: PCT/FI2013/050160
§ 371 (c)(1),
(2) Date: Aug. 14, 2014

(87) PCT Pub. No.: WO2013/121107
PCT Pub. Date: Aug. 22, 2013

(65) Prior Publication Data
US 2015/0012225 A1    Jan. 8, 2015

(51) Int. Cl.
*G06F 19/00*    (2018.01)

(52) U.S. Cl.
CPC ........ *G06F 19/3431* (2013.01); *G06F 19/345* (2013.01); *G06F 19/3487* (2013.01)

(58) Field of Classification Search
None
See application file for complete search history.

(56) References Cited

U.S. PATENT DOCUMENTS

| 2003/0135095 A1* | 7/2003 | Iliff ...................... A61B 5/0002 600/300 |
| 2005/0144042 A1 | 6/2005 | Joffe et al. |
| 2017/0169352 A1* | 6/2017 | Loetjoenen ............ G06N 7/005 |

FOREIGN PATENT DOCUMENTS

| WO | 2009130382 A1 | 10/2009 |
| WO | 2011161301 A1 | 12/2011 |

* cited by examiner

*Primary Examiner* — Tung Lau
(74) *Attorney, Agent, or Firm* — Ziegler IP Law Group, LLC

(57) ABSTRACT

The present disclosure relates to a method, apparatus, system and computer program for inferring a system state over time. Biomedical measurement data is obtained, wherein the data relate to at least one indicator of a system of interest and includes at least two indicator values being indicative of the state of the system of interest and the indicator values are measured at different time points. At least one measure of goodness for the indicator is formed by using values of the indicator of at least one control state and at least one comparison state. Difference values are formed for at least two indicator values with reference to the control and comparison states, and using the at least two difference values a change in value of said indicator is displayed with a progress indicator so that the change over time can be used in inferring the system state. The progress indicator has at least one dimension depending on the value of the at least one measure of goodness.

17 Claims, 8 Drawing Sheets

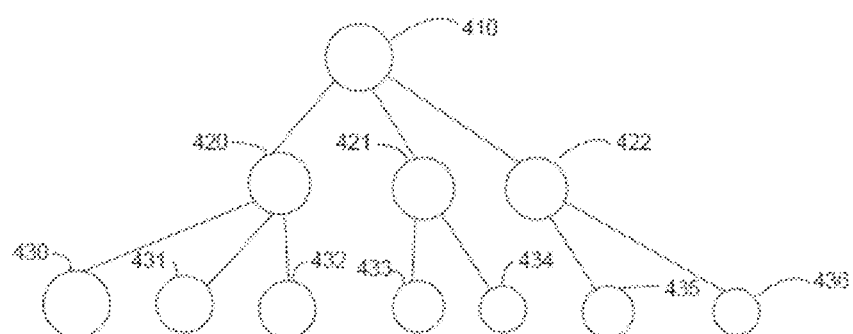
Fig. 4a
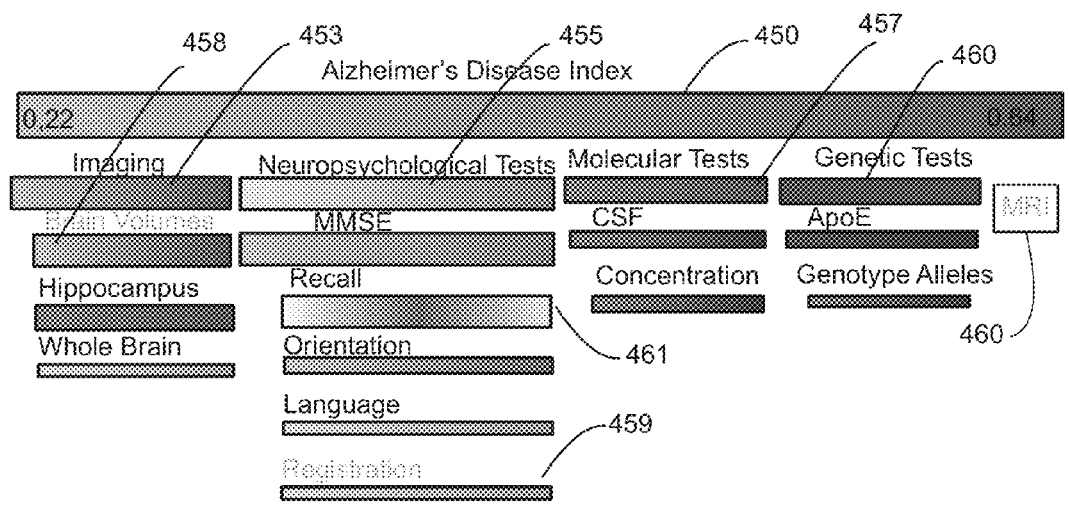
Fig. 4b
Fig. 4c
Fig. 4d

INFERRING A STATE OF A SYSTEM OVER TIME

FIELD

The aspects of the present disclosure relate to a method of inferring the state of a system over time. The aspects of the present disclosure relate to an apparatus and a system for inferring the state of a system over time and visualizing the state. The aspects of the present disclosure relate to the computer program product for inferring the state of a system over time and visualizing the state.

BACKGROUND

Any arbitrary system of interest can have at least two states. The system of interest can be, for example, a human body. Typically, the system of interest either functions correctly i.e. a healthy state or has an error i.e. an unhealthy state. There may be several healthy and/or unhealthy states i.e. the number of the healthy and unhealthy states may be large. For example, a patient may still be healthy even if there exists some suggestion about possible progressive disease or the state of disease may vary from slight to serious. The state of the system of interest defines which healthy or unhealthy state the patient is in and how much the state of the system of interest differs from a control state specified beforehand. In medical applications the state of the system of interest defines the disease a patient has and how far the disease has advanced, as compared with the normal, healthy state.

Computerized methods are needed in the above-mentioned analyses of the systems of interest to efficiently utilize multidimensional data and to find complex relations in the data. Each dimension of the data relates to an aspect of the particular system that is being measured (i.e. an indicator) and from which measurement values (indicator values) are gathered. Typically, the computerized methods give only a classification (healthy/unhealthy) as an output. However, in many applications the computerized methods cannot make the final decision because of possible erroneous measurements and uncertainty in the data, or merely because the computer cannot fully mimic the knowledge and experience of an expert. In such cases, a human user such as a doctor needs to make the final decision.

Nowadays, there is typically a large number of biomedical data available to the user interpreting the state of a system of interest. For example, different biomedical signals and images measured and results of various tests i.e. measurements may be available for the user to inspect. Some of these values and pieces of information may have additional information on the normal range of the value, and the user needs to observe this range in addition to the value itself. The different measured biomedical values data may be at least partially conflicting, and the data may be heterogeneous so that combining the data heuristically or numerically may be difficult and unreliable. Determining the state of the system may therefore be very time-consuming and prone to errors in interpretation.

There is, therefore, a need for solutions that make it faster, easier and less prone to errors to infer a state of a system of interest from obtained biomedical measurement data.

SUMMARY

Now there has been invented an improved method and technical equipment implementing the method, by which the above problems are alleviated. Various aspects of the disclosed embodiments include a method, an apparatus, a server, a client and a computer readable medium comprising a computer program stored therein, which are characterized by what is stated in the independent claims. Various embodiments of the invention are disclosed in the dependent claims.

The aspects of the disclosed embodiments relate to a method, apparatus, system and computer program for inferring a system state over time. Biomedical measurement data are obtained, wherein the data relate to at least one indicator of a system of interest and comprises at least two indicator values being indicative of the state of the system of interest and the indicator values are measured at different time points. At least one measure of goodness for the indicator is formed by using values of the indicator of at least one control state and at least one comparison state. Difference values are formed for at least two indicator values with reference to the control and comparison states, and using the at least two difference values a change in value of said indicator is displayed with a progress indicator so that the change over time can be used in inferring the system state. The progress indicator has at least one dimension depending on the value of the at least one measure of goodness.

Various embodiments relate to methods, apparatuses, systems and computer program products as follows. A part of the progress indicator may be selected, and details of indicator at said part of the progress indicator viewed. The progress indicator may be a gradient filled bar, which height and/or length depends on the at least one measure of goodness value for said indicator. The progress indicator may comprise beans indicating said difference values, wherein said beans are arranged next to each other and wherein height and/or length of at least one bean depends on the at least one measure of goodness value for said indicator. The progress indicator may have at least two different heights or lengths corresponding to different said measure of goodness values and different time instances. The obtained data may relate to at least one further indicator of the system of interest and comprise at least two further indicator values being indicative of the state of the system of interest and the further indicator values are measured at different time points, a measure of goodness is formed for said further indicator by using values of said further indicator of a control state and at least one comparison state, difference values are formed for said at least two further indicator values with reference to said further control and comparison states, a composite indicator of said indicator and said further indicator is defined, a measure of goodness is formed for said composite indicator by using information indicative of said measure of goodness of said indicator and said further indicator, difference values are formed for the composite indicator in a system of interest, and the composite indicator is arranged to be used in inferring the state of the system of interest. Progress bars may be arranged to be displayed on the basis of the measure of goodness value.

DESCRIPTION OF THE DRAWINGS

In the following, various embodiments of the present disclosure will be described in more detail with reference to the appended drawings, in which

FIG. 4a illustrates propagation of the measures of goodness and/or the difference values in a tree-like representation of indicators according to an example embodiment;

FIG. 4b illustrates ordering of the indicators according to the measure of goodness;

FIG. 4c illustrates refinement of the representation and visualization where indicators may be omitted from the state inference;

FIG. 4d illustrates progress indicator with varying measure of goodness indicated by the height of the bar;

DETAILED DESCRIPTION OF THE EMBODIMENTS

Figure 1:
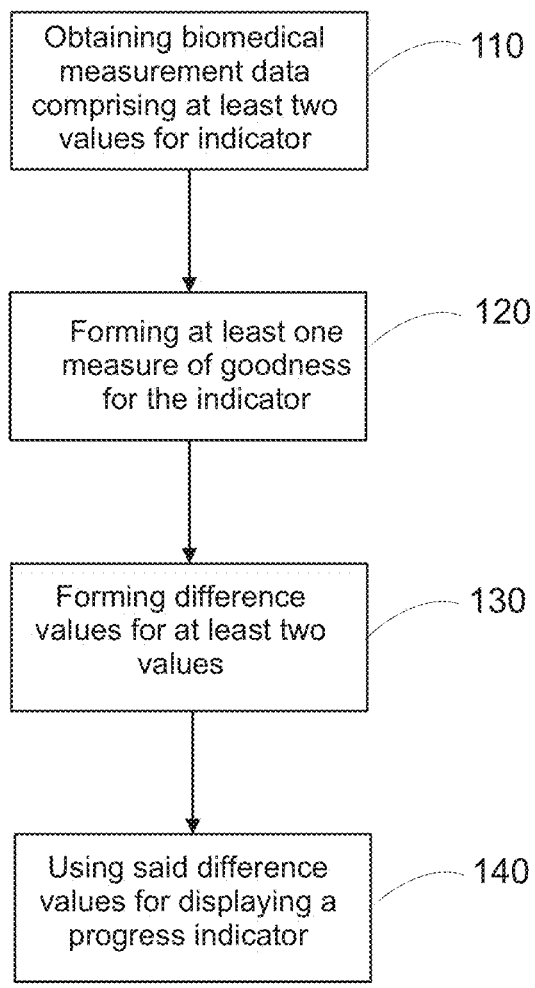
FIG. 1 shows a method for inferring the state of a system of interest according to an example embodiment of the present disclosure.

It has been noticed in the aspects of the present disclosure that time based databases of complex systems comprising longitudinal heterogeneous data, such as values of biomedical measurements collected over a time, often contain information that is not immediately obvious to the observer, for example a doctor or a researcher. It has also been noticed in the aspects of the present disclosure that there may be a need for novel decision support systems utilizing time based heterogeneous biomedical data that would benefit from a solution like the present invention to analyze available time based biomedical data and visualize analysis results as a function of time for quick understanding of indicators in question. It has also been noticed that the aspects of the present disclosure is applicable to handling of other heterogeneous data and their time development such as process data e.g. from paper manufacturing, various measurement data e.g. in environmental technology or agriculture, and so on.

The aspects of the present disclosure may offer, among other embodiments, a data visualization method for heterogeneous biomedical indicator values of a system of interest so that it is possible to follow the progress of a state of the system of interest longitudinally, over time. Biomedical measurement data to be analyzed relates to at least one indicator of a system of interest, i.e. a patient, and comprises at least two indicator values being indicative of the state of the system of interest and wherein said values are measured at different time points. In a set of related databases, information that can be quantified and represented as indicators (indicator values can be e.g. numeric values, classifying values, and free text using text mining methods) may be used for building two or more classes representing divergent states of a system. Based on classification criteria, some of these may be chosen to be control states and the others may be comparison states. Indicator values belonging to comparison states may be compared statistically to the indicator values of the control states to find statistical differences between the states and also the statistical significance of the difference. Progress of indicator may be inferred from biomedical data comprising at least two records of biomedical measurements (indicator values) collected over a time and may be visualized by a bar structure or any other suitable structure so that the expert may more easily see how the measured indicator settle compared to control and comparison states in its part of the timeline i.e. in the time point that it was measured, and how indicator progresses i.e. changes states over time, but also how significant and how reliable is the difference between the visualized progress indicator and the control and comparison states.

Progress indicators may also be organized in a hierarchy for visualization where the expert may additionally compare a single system of interest to the control and comparison states for inferring its state, i.e. to discover indicator values, probabilities, or other measures that are reflecting the belonging of the system of interest to different control and comparison states.

In addition, the state of a system may be re-evaluated and visualized whenever additional longitudinal data i.e. additional measurement data become available. Thus possible changes in measurement data can be clearly be observed from progress indicator bar.

FIG. 1 shows a method for inferring the state of a system according to an example embodiment of the present disclosure. The aspects of the present disclosure enable inferring the state of a system of interest (a patient) from a set of indicators determined or measured from the system of interest. The analysis may be carried out by comparing data from the system of interest with the data in the databases of at least one control state (e.g. a normal state) and at least one comparison state (e.g. a unhealthy state) using statistical methods. The database of a state includes data from at least one example of a system that is known to be in a particular state. One state, either a real or a synthetic state, may be selected as a control state. For example, if the system is a human brain and one control state is a healthy state, the database of the healthy state contains measurement values (i.e. indicator values) from at least one healthy brain describing, for example, the anatomy and/or function of the healthy brain. Another comparison state, an error state, may be a brain disease, and the database of the comparison state contains measurement values from at least one person with the brain disease. The databases may also be a single database which includes all available information for all states pertaining to the context. For the clarity of description, the term 'database' is used for denoting both a single database containing all information about all states and several databases containing this information as entirety.

In phase 110, biomedical measurement data from a system of interest is obtained. The biomedical measurement data relates to at least one indicator of a system of interest and comprises at least two indicator values being indicative of the state of the system of interest and wherein indicator values are measured at different time points. Indicator values for at least one control state and at least one comparison states are retrieved from a database using the different data available for the states. In phase 120, measures of goodness for indicators are formed by using values of said indicators of at least one at least one control state and at least one comparison state. The measure of goodness indicates, as an index number, how significant or reliable the indicator is in differentiating between control and comparison states. Measures of goodness for an indicator may be computed differently at different time points, and may thus have different values at different time points. The measure of goodness is defined from data available in the database about the control and comparison states, i.e., the measures of goodness may be independent of the indicator values defined for the system of interest being studied. In phase 130, difference values for at least two indicator values are formed with reference to the control and comparison states. The difference value indicates, with regard to the indicator, the distance of the system of interest from the control and comparison states, or may indicate a relative distance of the system of interest between control and comparison states, or may indicate probabilities of whether the system of interest belongs to control or comparison states. In other words, a difference value gives indication to how probable it is that the system of interest is in a particular control i.e. healthy or comparison i.e. unhealthy state. The difference value, or other computed values, may also describe how distinct the state of the system of interest is. The difference value may also be computed in some other manner than those presented above, as long as it indicates the relationship of the system of interest to the control and comparison states.

In phase 140, at least two difference values are used in displaying a change in value of said indicator with a progress indicator so that the change in value of said indicator over time can be used in inferring the system state, and wherein the progress indicator has at least one dimension depending on the value of the measure of goodness, one dimension depending on the difference value, and one dimension depending on the time. For example, the thickness and/or height and/or length and/or color of the bar may depend on the measure of goodness, difference value, or time. Difference values may be displayed next to each other as a function of time, longitudinally, for example, as a bar structure. The bar may comprise at least two difference values that are indicated, for example, by colors, wherein each color represents certain difference value i.e. difference values are color-coded. In addition, difference values may be indicated as a part of the bar i.e. as a bean (see FIG. 5*a*). Beans are arranged next to each other so that each bean forms a part of the bar structure. The size i.e. dimensions of the bean i.e. length and/or height may depend on the measure of goodness of the indicator. If the value measure of goodness is large, the bean may also be high and long i.e. the large measure of goodness value may be indicated by large beans and small values by small beans. The bar may also be gradient filled by colors of difference values (see FIG. 5*b*). The value of measure of goodness may also effect the altitude dimension of the gradient filled bar, but it may also effect to the length dimension of the bar.

Possible change/s in difference values and change/s in patient state over time can clearly seen from the progress indicator bar on the base of colors and possible included difference values. In addition, changes in the indicator values over time may be more important than the latest indicator values available. The dependence of the size of the progress indicator from the measure of goodness helps in inferring the state so that the human may concentrate on the most significant indicators more easily. In addition, it is possible to display the progress indicators in a hierarchical manner (see FIG. 4*c*) and may be reordered to offer additional insight for inference and to emphasize measures of goodness and/or difference values. In this phase, the progress of the difference values and the measures of goodness may be used for inferring the state.

After phase 140, the state may be inferred by the system, by the user or by both so that he/she can determine the state of the system of interest.

In the following, several further embodiments of the present disclosure will be described in the context of determining the states of a human being over time. For the remainder of this document we will use an example dataset to clarify some aspects of the present disclosure. However, the present disclosure is not limited to the following example dataset containing medical data about patients who have been suspected or confirmed of having Alzheimer's disease (AD). Information in the database contains patient information (name, age, etc. . . . ), patient demographics information (years of education, occupation), Alzheimer's disease diagnoses, neuropyschological test results, magnetic resonance imaging (MRI) images of the brain with quantification results (e.g., region volumes), and AD biomarker information from cerebrospinal fluid (CSF) samples. We consider as a system of interest a person who comes to a memory clinic after his family has noticed problems in daily life due to mild memory problems.

Figure 2A:
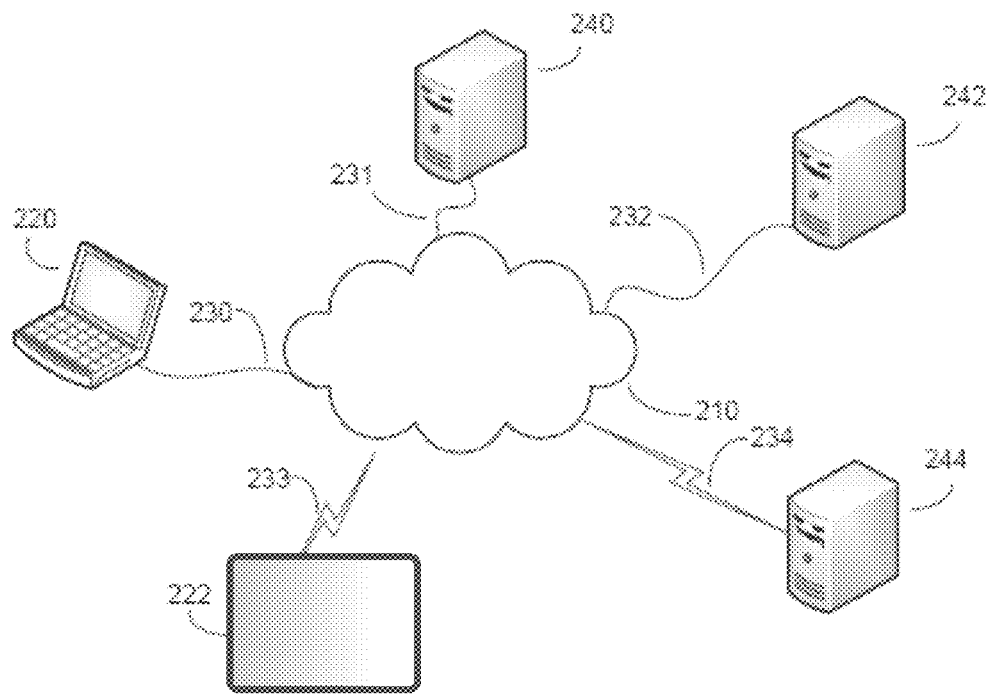
FIGS. 2a and 2b show devices and a system arranged to infer and/or display the state of a system of interest according to an example embodiment of the present disclosure.

FIG. 2*a* shows devices and a system arranged to infer and/or display progress of the states of a system over time according to an example embodiment of the present disclosure. The different devices are connected via a network 210 such as the Internet or a local area network or any wired or wireless communication network. There are a number of servers connected to the network 210, and here are shown a server 240 for offering a network service e.g. for classifying a system, a server 242 for storing datasets related to the service and a server 244 for processing data and performing computations. These servers may be made of multiple parts or they may be combined into one more servers.

There are also a number of end-user devices such as personal computers 220 and mobile devices 222. These devices 220 and 222 may also be made of multiple parts. The various devices are connected to the network 210 via communication connections such as a fixed connection 230, 231 and 232 or a wireless connection 233 and 234. The connections may be implemented by means of communication interfaces at the respective ends of the communication connection.

The various embodiments of the present disclosure may be implemented with the help of computer program code that resides in a memory and causes the relevant apparatuses to carry out the aspects of the present disclosure. For example, a personal computer may comprise circuitry and electronics for handling, receiving and transmitting data, computer program code in a memory, and a processor that, when running the computer program code, causes the computer to carry out the features of an embodiment. Yet further, a server may comprise circuitry and electronics for handling, receiving and transmitting data, computer program code in a memory, and a processor that, when running the computer program code, causes the server to carry out some or all of the features of an embodiment.

Figure 2B:
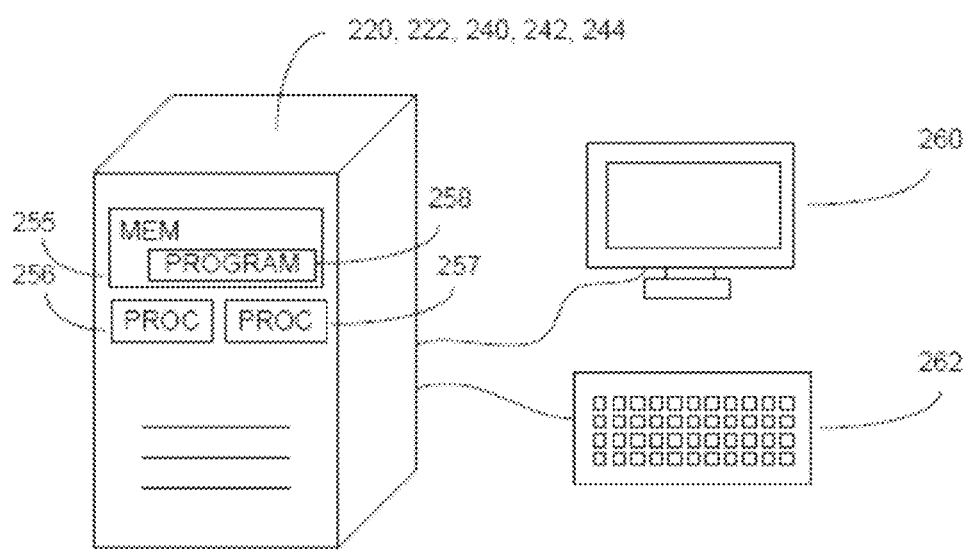

FIG. 2*b* shows a device arranged to infer and/or display progress of the states of a system over time according to an example embodiment. As shown in FIG. 2*b*, the device 220, 222, 240, 242 or 244 contains memory 255, one or more processors 256, 257, and computer program code 258 residing in the memory 255 for implementing, for example, computations for inferring the state of the system. The device may also be functionally connected to a display 260 for example for displaying the system indicators according to an embodiment. There may also be various input means functionally connected to the device, such as a keyboard 262, speech command interface, data gloves, and different communication interfaces for receiving input (not shown).

It needs to be understood that different embodiments allow different parts to be carried out in different elements. For example, storing the data sets, forming the indicators and displaying the indicators may be carried out entirely in one device or across multiple devices. For example, data may be stored in one device, the user input may be received by another device, and the computations may be carried out in a third device. The various functions of the present disclosure may be implemented as a software component residing on one device or distributed across several devices. A doctor in a hospital may use an embodiment running on the doctor's personal computer, connected to the hospital information system (HIS), drawing data from several servers in the hospital, e.g. an image server and a clinical investigations data server, and computing analyses locally. Another embodiment may be a web browser based solution remotely accessed over the Internet, where the system of interest is described by a user entering indicators in a web form which would then perform data retrieval from some server, data analysis on another, and visualization of the results inside the web application.

There may be several phases to the present disclosure. Such phases may be 1) indicator value sampling (i.e. forming of control and comparison states from available data), 2) indicator value analysis (i.e. computing measures of goodness for indicators and/or difference values for the system of interest), 3) determining the overall state of the system of interest in several contexts (i.e. determining its composite difference values) 4) feature re-ordering for visualization (e.g. based on the measures of goodness), and 5) dynamic refinement of the visualization (e.g. due to new available data or user interaction). These phases are described later in context with the respective example embodiments.

Sampling is the process of forming control and comparison states from available data. It should be noted that the selected states need not be exclusively the control state and the comparison state. Depending on the goals of the analysis and the sets of measurements, the states may be named in a different manner, e.g. state 1, state 2 etc. These states may correspond to the control state and to the comparison state, or not. The data used for constructing the states may be sparse, meaning that we may not have exhaustive collections of data or test results from all possible time points and/or measurable indicators. We may only have information that has been collected successfully. This issue may be taken into account during sampling, e.g. some indicators with missing data may be used as such, some may be pruned from the analyses if not enough data exists, and some may be handled with imputation, i.e., substituting some data for missing values. Also, in the progress indicators, values may be interpolated or extrapolated from existing values to those time instances where no indicator value is available.

There are several ways to do sampling (i.e. extracting data) from databases to form states. The following list includes some solutions for forming a state but is not exhaustive. 1) Take all data based on some criteria. 2) Take enough of data based on some criteria. 3) Stratified selection (i.e. choose data with some criteria that also matches a profile similar to the system of interest). In our example case, stratified sampling of states may be done by taking data of all patients who are of the same gender and age and had a similar degree of education when they were initially admitted for studies as our system of interest. From this data two states may be formed, one from those who were eventually diagnosed with Alzheimer's disease (i.e. comparison state) and the other from those who were healthy (i.e. control state). 4) Take the examples that differ most from another state. This can be done using Cartesian distance, Mahalanobis distance, or statistical tests. The number of indicator values selected for the states can be defined using a constant number, or a threshold for the distances or the results of the statistical tests. The outliers may also be detected and removed from the states. 5) Generate synthetic collections of indicator values that represent the states possibly adhering to a statistical description of the data, e.g. mean and standard deviance. 6) Generate resampled collections by selecting representative indicator values for the control and comparison states. For example, for each measurement, the N most extreme indicator values are searched. The largest values are searched if the indicator values of the state are larger than the values of a comparison state, and respectively the smallest values are searched if the indicator values in the state are smaller than in the comparison state. In addition to these, other sampling schemes may be used.

Figure 3:
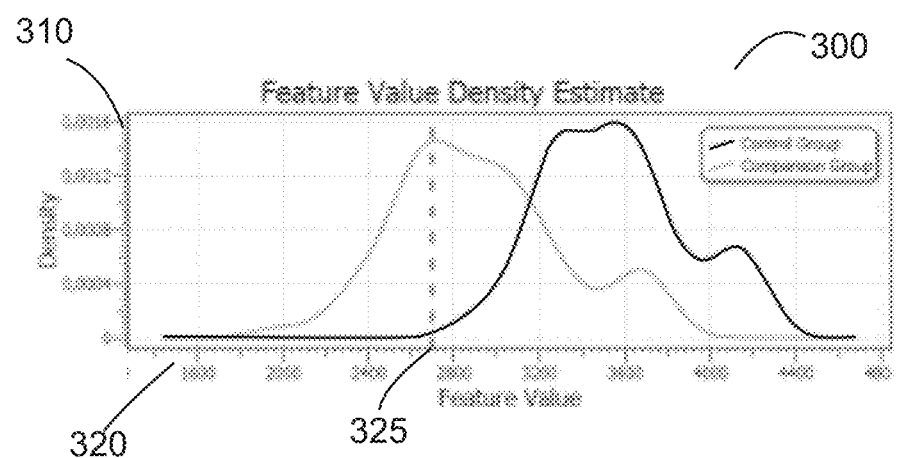
FIG. 3 shows a representation and visualization of probability distributions for a control and comparison state and illustrates visualization of the state of the system of interest according to an example embodiment.

FIG. 3 shows one indicator after sampling using a representation of probability distributions for control and comparison groups. It also illustrates visualization of an indicator from a system of interest according to an example embodiment. This information about a sampled indicator and its distribution may be shown to the user e.g. as a graph 300. In FIG. 3, density estimates 330 and 335 are shown. These density estimates indicate an estimated probability density 310 of an indicator 320. In other words, if a certain indicator value 320 has a high density value 310 according to the density function, the indicator value 320 is likely to appear in data. If the value is low, it is less likely that such a value for the indicator would appear. Accordingly, the shapes of the density functions 330 and 335 indicate which values are more probable for the control and comparison states. For example, it is clearly more likely that an indicator value from a system of interest 325 of approximately 2700 would belong to the comparison state than the control state. Measure of goodness and difference value for the indicator in question may be determined from the data used in the visualization by e.g. distance measures or probabilistic measures as defined below.

During sampling two or more states which include some or all available indicators (and indicator values) are constructed from a dataset matching the sampling criteria. Indicator value analysis may now be performed for each individual indicator, i.e. measures of goodness may now be computed for the indicators to determine which indicators have differing values in a control state and a comparison state, and therefore, which indicators may give reliable information on the particular state. Indicator values may also be verified at this point to satisfy any assumptions, e.g. scalar indicators may be checked to be normally distributed (for example with Kolmogorov-Smirnov test). In addition, indicators whose sample data does not differ between states may at this point be eliminated from further analysis. Depending on the type of each indicator, measure of goodness computation may be done in different ways, as long as the measure of goodness provides statistical information about the separation between the two groups.

One possibility to determine the measure of goodness is to use statistical tests (e.g. t-tests for scalar values and chi-square test of independence for nominal values). One of the control states and one of the comparison states are used in the statistical test. The result of the statistical test is a p-value that describes the probability that the differences in the indicator values between the control state and the comparison state are the result of chance alone. Therefore, the smaller the p-value the more probable it is that there are real differences in the indicator values between the control state and the comparison state. From the p-values of the $i^{th}$ indicators, $p(i)$, the measure of goodness, $S(i)$, may be computed for the indicators:

$$S(i) = \frac{\ln\min[p(i), 0.05] - \ln 0.05}{\ln 0.000001 - \ln 0.05}.$$

The measure of goodness value S(i) is zero, if the p-value is larger than 0.05 (i.e., if there are no statistically significant differences in the control and comparison states), and it increases as the differences between the control and comparison states become larger. Alternatively, the measure of goodness could be the classification accuracy, computed e.g. using cross validation, when using the given indicator to classify control and comparison sample cases to control and comparison states. Measure of goodness may also be computed by finding a suitable indicator value separating the control and comparison states, and by using the said separation value as a decision threshold for computing the classification accuracy from indicator values in control and comparison states. These methods for computing the measure of goodness are only examples and the computation could be implemented in many other ways.

By utilizing the sampled control and comparison states, in addition to measures of goodness, difference values may now be computed for the indicator values of the system of interest. These give information about the state of the system of interest in regards to individual indicator values obtained from the system of interest. Difference value computation can be done using e.g. distance measures or probabilistic measures.

A relative distance from the control state to the system of interest, when compared with the comparison state, may be calculated as:

$$d(i) = \frac{m(i) - \overline{m}_R(i)}{\overline{m}_S(i) - \overline{m}_R(i)},$$

where m(i) is the $i^{th}$ indicator of the system of interest, $\overline{m}_R(i)$ is the mean or median of the control state, and $\overline{m}_S(i)$ is the mean or median of the comparison state. The d(i) value shows how large the difference between the indicator value from the system of interest and the control state is, and which is the direction of the difference.

In a probabilistic measure, it is studied how the indicator values of the system of interest fit to the distributions of the corresponding indicators of the control and comparison states. Let us consider the case where $\overline{m}_R(i) < \overline{m}_S(i)$. The cumulative probabilities:

$P_R(i) = P(m_R(i) \geq m(i))$ and $P_S(i) = P(m_S(i) \leq m(i))$ are determined from the system data, where $m_R(i)$ and $m_S(i)$ denote the distributions of indicator values of the control and comparison states, respectively, $\overline{m}_R(i)$ is the mean or median of the control state, and $\overline{m}_S(i)$ is the mean or median of the comparison state. In other words, it is studied how probable it is that a system in the control state has an indicator value larger than the corresponding value of the system interest, and vice versa for the comparison state. The cumulative probabilities can be determined with any method, for example, using the Gaussian approximation or un-parametric methods. Alternatively, the normal probabilities, instead of cumulative probabilities could be used:

$P_R(i) = P(m_R(i) \cong m(i))$ and $P_S(i) = P(m_S(i) \cong m(i))$.

A difference value for the indicator value m(i) of the system of interest may then be obtained from:

$$f(i) = \frac{P_S(i)}{P_S(i) + P_R(i)}.$$

The difference value f(i) describes how well an indicator value m(i) of the system of interest fits to the distributions of the control and comparison states. The larger the value is the better the indicator value of the system of interest fits to the distribution of the comparison state. The difference value may obtain values between zero and 1. The value of 0.5 represents the case in which it is equally probable that the indicator value arises from a system having a state corresponding to the control state or to the comparison state.

In case $\overline{m}_R(i) > \overline{m}_S(i)$, the probabilities $P_R(i) = P(m_R(i) \leq m(i))$ and $P_S(i) = P(m_S(i) \geq m(i))$ are determined. Otherwise the analysis proceeds as presented above.

Difference values may be computed by using other methods than presented here. Other methods may produce a specific range of difference values or the difference values may be extrapolated after the fact so that values smaller than zero or difference values larger than 1 are possible.

For an example of measures of goodness and difference values, in the example dataset, may be found that delayed recall tests of the Mini Mental State Examination and volume of hippocampus computed from MRI images classify relatively well between healthy and AD patients in our control and comparison states, i.e. these indicators have a high measure of goodness. If difference values of these indicators in a patient show a high correspondence to AD state, this information may be used to determine that the patient has high probability of actually having AD.

In FIG. 4a, the root node 410 has three child nodes 420, 421, 422. The root may have any number of child nodes of any kind. The child nodes may be intermediate nodes (composite indicators) such as in FIG. 4a, or they may be outer nodes (indicators) so that they do not themselves have any child nodes. In FIG. 4a, the root node 410 has 10 descendant nodes 420, 421, 422, 430, 431, 432, 433, 434, 435, 436. In FIG. 4a, the node 420 has in turn three child nodes 430, 431 and 432, and these child nodes are leaf nodes (indicators). The node 421 has two child nodes 433 and 434 and the node 422 has two child nodes 435 and 436. The nodes (indicators) may have a difference value or another value assigned to them implying to which state the system of interest belongs to. The nodes may also have a measure of goodness value assigned to them. The difference values and the measure of goodness values may be propagated from the leaf nodes to the intermediate nodes and further from the intermediate nodes to the root node. There may be any number of levels in the tree, and all the branches may be of same depth or they may be of different depth.

In FIG. 4b, the different progress indicators comprising difference value beans have been ordered according to their measure of goodness value (indicated by the height of the bean i.e. lateral size 444). Progress indicators are visualized in a function of time by adding time as a further component. According to an embodiment the visualization that incorporates time divides time to slots (beans) of particular length and displays these as multiple time points which in this embodiment comprises four time points a, b, c, d. Progress indicators comprises data from four measurements that are performed at mentioned points in time a, b, c, d. The oldest data i.e. the data that is measured at earliest point in time a is disclosed in the first end i.e. the left end of the progress indicator and the most recent data d in the second end of the progress indicator i.e. the right end of the progress indicator. As the measurement process advances, changes in data will change the state index and the change can be observed from changes in the progress indicators. The most significant indicator is the Recall progress indicator 440, followed by the Orientation progress indicator 441. The Recall progress indicator 440 also shows clearly that the system of interest is likely to belong to the normal state (the most recent difference value is 0.15), but Recall progress indicator 440 also clearly indicates that the difference value has not much changed over a time. Whereas the Orientation feature has larger difference values and also the most recent difference value is larger. The larger difference values of Orientation progress indicator 441 is disclosed also by colors and also changes in state of Orientation progress indicator 441 are visualized by color changes. In this embodiment, the darker color represents the larger difference value. The changes of difference value from smaller to larger may also indicate change from healthier state towards unhealthiest state. The Language feature progress indicator 442 and the Additional information feature progress indicator 443 have a small classifying power, and they appear downwards in the representation from the more powerful indicators.

Reordering nodes based on the measure of goodness or difference value may be implemented with the following pseudo code:

```
FUNCTION reorder_nodes(LIST<NODE> nodes, ORDER order)
  1:  FOR EACH node IN nodes
  2:    reorder_node(node, nodes, order)
FUNCTION reorder_node(NODE node, LIST<NODE> nodes, ORDER order)
  1:  IF order = ORDER::GOODNESS
  2:    var ordered_nodes = nodes.ORDER_BY_DESCENDING(n => n.goodness))
  3:  ELSE IF order = ORDER::DIFFERENCE
  4:    var ordered_nodes = nodes.ORDER_BY_DESCENDING(n => n.difference))
  5:  VAR old_index = nodes.INDEX_OF(node);
  6:  VAR new_index = ordered_nodes.INDEX_OF(node);
  7:  IF (old_index != new_index)
  8:    nodes.MOVE(oldIndex, newIndex);
```

In the code, node will be relocated in the list of nodes and nodes contain all the nodes of the same category, including the node to be relocated. Other ordering modes are also possible for implementation, for example ordering by increasing difference value.

FIG. 4c illustrates refinement of the representation and visualization where progress indicators may be omitted from the state inference. In the user interface a user may be able to select which indicators are allowed to affect the analysis. This may be arranged by providing a means to remove a progress indicator node from the comparison and propagation phase. After a node has been removed, the difference and/or measure of goodness values may be computed again, ignoring any indicators that were removed. Any changes may immediately affect the visualization to make it reflect the updated state. This feature allows experts to focus on nodes they find interesting or deem important in making the final inference and/or classification.

In FIG. 4c, there is a visualization of a case where several nodes have been excluded from the computation. As shown earlier, there are a number of indicators below the top progress indicator 450. Some of progress indicators (left end of the progress indicators) like Imaging 453 and Molecular tests 457 indicate by dark color that those indicator values from the system of interest are more closely related to the comparison (i.e. error) state, while some like Neuropsychological tests 455 indicate towards the normal state. Therefore, in the figure, neuropsychological tests suggest that the patient is in normal state, while other evidence is indicating the opposite. The left end of the top progress indicator 450 is leaning towards unhealthy state due to more statistic significance (i.e. larger measure of goodness value) from imaging, molecular tests and genetic tests combined. As can be seen from the top progress indicator 450, the total difference value has changed (indicated by change of color intensity) its state over time. The oldest measurements (left end of the top progress indicator 450) indicates healthy and the most recent (right end) unhealthy state.

It is also possible that progress indicator stays constant in every measurements over time, this is shown, for example, in FIG. 4c as Genetic Test progress indicator 460, where the difference value stay constant over time as 0.85. In addition, difference value may also change from low to higher and again to lower level or vice versa, one example is shown, by Recall progress indicator 461 in FIG. 4c, wherein difference values changes from 0.15 to 0.45 and back to lower level to 0.23.

In FIG. 4d, there is another type of progress indicator. The progress indicator changes its height to represent changes in the measure of goodness, and discontinuous section representing discontinuities in the data is indicated by a gap 470 or by a split 470. The measure of goodness may change over time e.g. if the reference groups and/or their statistics change. Gradient indicates difference values of measurements, which difference values are changed over time to indicate a state of the system such as progress of disease at that certain time point.

In this embodiment, difference values of measurements are represented in progress indicators by colors in a linear gradient manner. Lighter color intensity represents healthy state and darker intensity unhealthy state. However, it is possible to use some other colors to indicate states or use numbers like difference values or some symbols to indicate change of state and/or stage of difference value. In addition to colors representing difference values, it is possible to include difference value to progress indicators, for example, all the defined difference values over time or, for example, the first and the most recent difference value like in the top progress indicator 450. Some of the nodes are included in the computations and visualization like, Imaging 493, Neuropsychological tests 455 and Molecular Tests 457 while others have been removed like Brain Volumes 458, Registration 459 and MRI.

It is possible that measurements of the patient at different time points do not contain same measurement data (i.e.

measurements of the same indicators) and thus may have different indicator values available. However, it is possible to visualize progress indicator, such as the top composite progress indicator 450, only on the basis of data that is available in each measurement. Also, in the progress indicators, values may be interpolated or extrapolated from existing values to those time instances where no indicator value is available.

Computation of composite measures of goodness may be done with several methods and protocols. Measures of goodness from the child or descendant nodes or indicator values from child or descendant nodes may be used for the computation of composite measures of goodness. Methods for computing measures of goodness from child or descendant nodes include, among others: 1) selecting the largest measure of goodness; 2) using correct classification rate of control and comparison states as the measure of goodness; and 3) combining of indicator p-values. Several methods for computing a composite measure of goodness from child or descendant nodes are presented as pseudo code in the following. Composite measure of goodness could also be computed using other methods, not presented here.

In the maximum measure of goodness method, composite measure of goodness is chosen from the child or descendant node with the largest value, as indicated by the pseudo code below.

```
FUNCTION max_goodness(LIST<NODE> nodes)
RETURNS (goodness)
  1: VAR goodness = nodes.MAXIMUM(node => node.goodness)
  2: RETURN (goodness)
```

Line one (1) selects the maximum value from measures of goodness in the nodes list, which is returned on line two (2).

In correct classification rate method, a combined difference value is computed with some method for each sample case in the control and comparison states. Using e.g. cross validation, these difference values are used for getting the correct classification rate (CCR) which is set as the measure of goodness for the composite indicator.

```
FUNCTION ccr_goodness(LIST<NODE> nodes)
RETURNS (goodness)
  1: FOR EACH sample IN control_state, comparison_state
  2:   diff[sample] = GET_COMPOSITE_DIFFERENCE(sample, nodes)
  3: VAR goodness =
       GET_CORRECT_CLASSIFICATION_RATE(diff)
  4: RETURN(goodness)
```

On line two (2) a method is called which computes a difference value for a sample from the control or comparison state, difference value computation methods are presented later. This method is called for each training sample due to the loop construct on line one (1). After all difference values for samples in the control and comparison states have been obtained, a method is called on line three (3) to compare them to correct classifications, known for the training set. Composite measure of goodness is then set as the correct classification rate.

In combined P method, the measure of goodness is computed from a weighted average of p-values that have been computed for child or descendant nodes. Weighting of the computation is obtained from difference values of the system of interest in the child or descendant nodes. The method may be implemented by combining the child or descendant nodes' underlying p-values with e.g. Stouffer's method. This is illustrated in the pseudo code below.

```
FUNCTION combine_p_goodness(LIST<NODE> nodes)
RETURNS (goodness)
  1: VAR total_z = 0
  2: FOR EACH node IN nodes
  3:   VAR z = GET_Z_SCORE(node.p_value)
  4:   total_z += (node.difference - 0.5) * z
  5: total_z /= SQRT(nodes.SUM(node => (node.difference - 0.5) ^ 2))
  6: VAR goodness =
       GET_GOODNESS_FROM_P(GET_P_VALUE(total_z))
  7: RETURN (goodness)
```

On line three (3), p values of indicators are converted to z scores, which are weighted by the node difference on line 4 and added to a total z score, as defined in Stouffer's method. Combined z score is obtained by dividing the total weighted z score by the square root of the sum of squared weights, which is then converted to a p value and used for getting the measure of goodness, using e.g. method presented on page 9.

Logistic regression and principal component analysis (PCA) may also be used in the propagation of measure of goodness values to composite indicators. Instead of using all indicators from child or descendant nodes, a PCA projection is used to find indicators which define the composite indicator well. The measure of goodness is then determined e.g. by using logistic regression to evaluate the PCA projections' ability to classify sample cases from control and comparison states, as shown in pseudo code below.

```
FUNCTION pca_log_reg(LIST<NODE> nodes)
RETURNS (goodness)
  1: VAR pca = PCA(nodes.control, nodes.comparison)
  2: VAR diff = LOG_REG(pca, nodes.control, nodes.comparison)
  3: VAR goodness =
       GET_CORRECT_CLASSIFICATION_RATE(diff)
  4: RETURN (goodness)
```

First, a PCA projection from the indicators is obtained on line one (1). This projection or mapping of multiple indicators into fewer indicators may be done using other methods as well. Difference values are computed for the samples in control and comparison states on line two (2) using this time logistic regression. After all difference values for samples in the control and comparison states have been obtained, a method is called on line three (3) to compare them to correct classifications, known for the training set. Composite measure of goodness is then set as the correct classification rate.

As was the case with composite measures of goodness, composite difference values may also be computed using several methods. It should be noted that composite indicator values for control and comparison states or for the system of interest are not necessarily computed, since it may be impossible to combine multiple indicator values to a single composite indicator value in a sensible manner. Another matter to observe is that composite difference values computed using the methods presented below are conceptually different from difference value computation methods presented earlier. Previously presented difference value computation methods (that were presented using indicator values) may be applied to the results from composite difference value computation methods to get composite difference values conceptually identical to difference values computed from the indicator values.

Composite difference values, i.e. the difference value for composite indicators, may be computed with e.g. weighted averaging, in which the indicator difference values are averaged with weightings that are the measures of goodness:

$$D = \frac{\sum_i S(i)f(i)}{\sum_i S(i)},$$

where S(i) is a function that computes the measure of goodness for an indicator and f(i) is a function that computes the difference value from an indicator value of the said indicator in a system of interest. The obtained value D describes how closely the indicator values of the system of interest match with the corresponding values in the comparison state. Logistic regression (sometimes called the logistic model or logit model) can also be used for prediction of the probability that the system of interest fits comparison system by fitting indicator values to a logistic curve, providing a composite difference value for the system of interest.

Composite difference may also be derived by first computing a difference value for the system of interest as defined above and then also computing difference values for all samples in the control and comparison states using the same method. Using the difference value of the system of interest against difference values from control and control states can be computed using the same methods that were presented for computing difference values from indicator values. Again, as with composite measures of goodness, the methods presented here for computing composite differences are not exhaustive, but other methods may also be used.

From tables containing numerical data of the indicators, measures of goodness, and difference values it may be difficult to perceive the most important differences between the different states or to compare a system of interest with the different states and most of all notice the direction of healthy, is it going down and if in which pace. On the other hand, the human visual system can effectively process information coded with colours and shapes and sizes of objects. Still, if there is a high amount of data coded with colours and shapes and sizes, it has been noticed in the present disclosure that the human visual system may get dis-oriented.

Figure 5A:
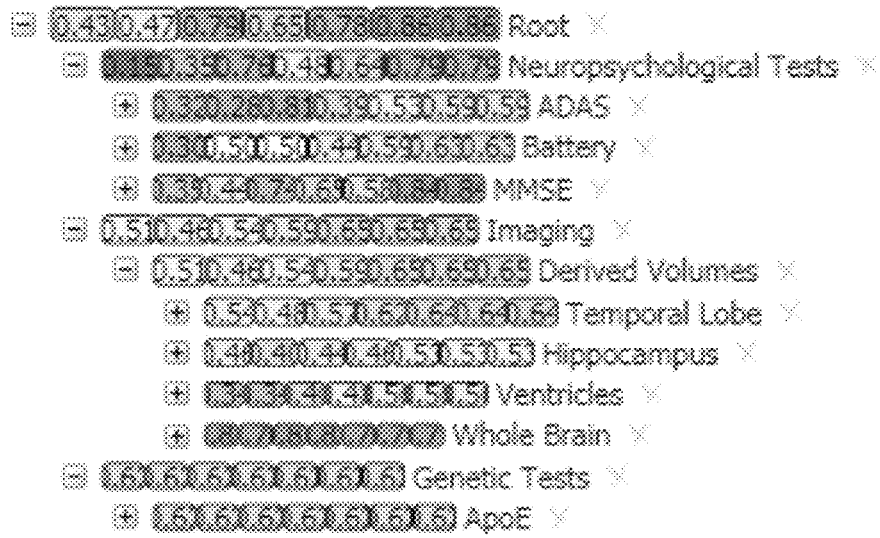
FIGS. 5a and 5b show representations and visualizations of progress indicators according to an example embodiment.
Figure 5B:
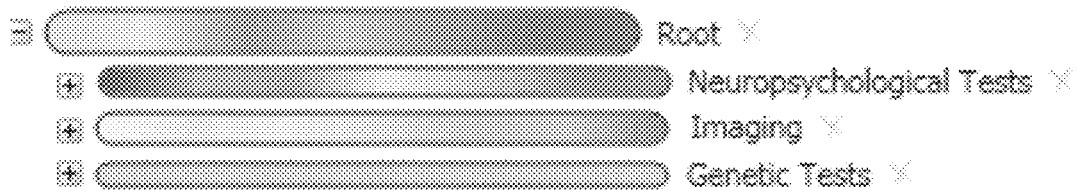

FIG. 5a discloses change in system state over time, which is shown in the changing values and colours and in FIG. 5b by gradientally changing colours representing the difference values. In FIG. 5b individual beans of FIG. 5a are replaced with a single multi-colour gradient bar showing the change in state index values linearly over time. FIG. 5b only discloses some of the bars of the FIG. 5a. From FIG. 5b is shown an embodiment, where difference values are changed from small difference value to larger difference value and back to small again. This is indicated by colours changing from light to darker and back to lighter again (see, for example, progress indicator of Root). In FIGS. 5a and 5b, difference values are indicated by different intensity stage of red and blue, wherein dark red means low difference value and dark blue high difference value. However, in FIGS. 5a and 5b, red and blue are shown by different intensity stage of grey.

Figure 6A:
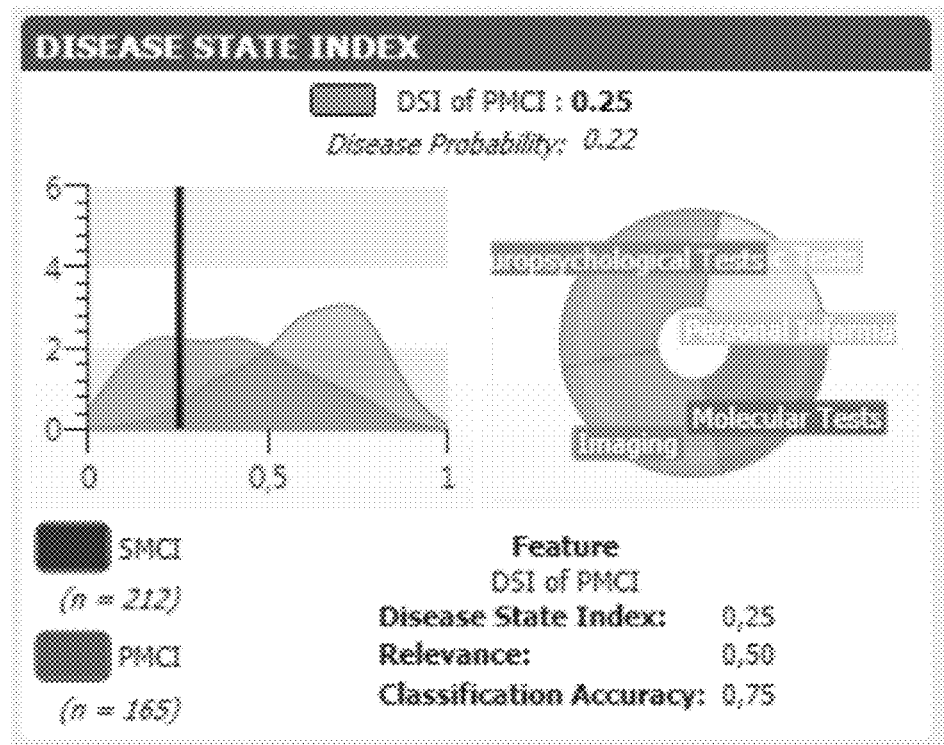
FIGS. 6a and 6b show detailed view of a time point of progress indicator indicators of FIG. 5a according to an example embodiment.
Figure 6B:
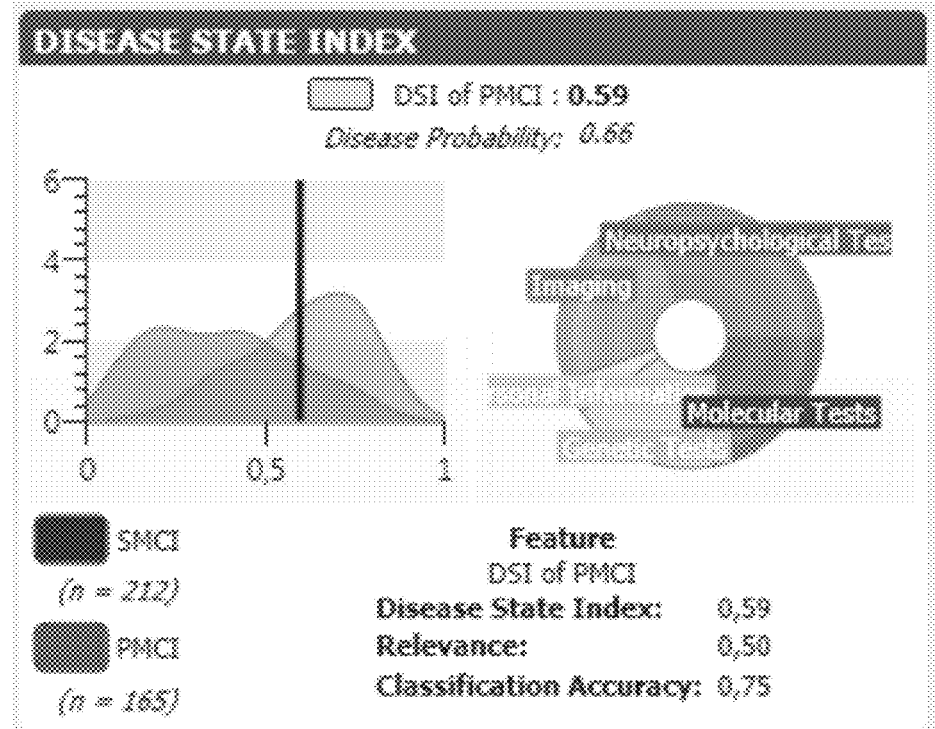

Selecting a node and time point in progress indicators of FIG. 5a can be shown the details for that particular bean of a current time point. This is shown in FIGS. 6a and 6b according to an embodiment of the present disclosure. Selecting a node and time point in this tree can show the details for that particular node. In FIG. 6a, user a top node near the start of measurements is selected and in FIG. 6b, root node at the final available point in time is selected.

Figures 7, 8:
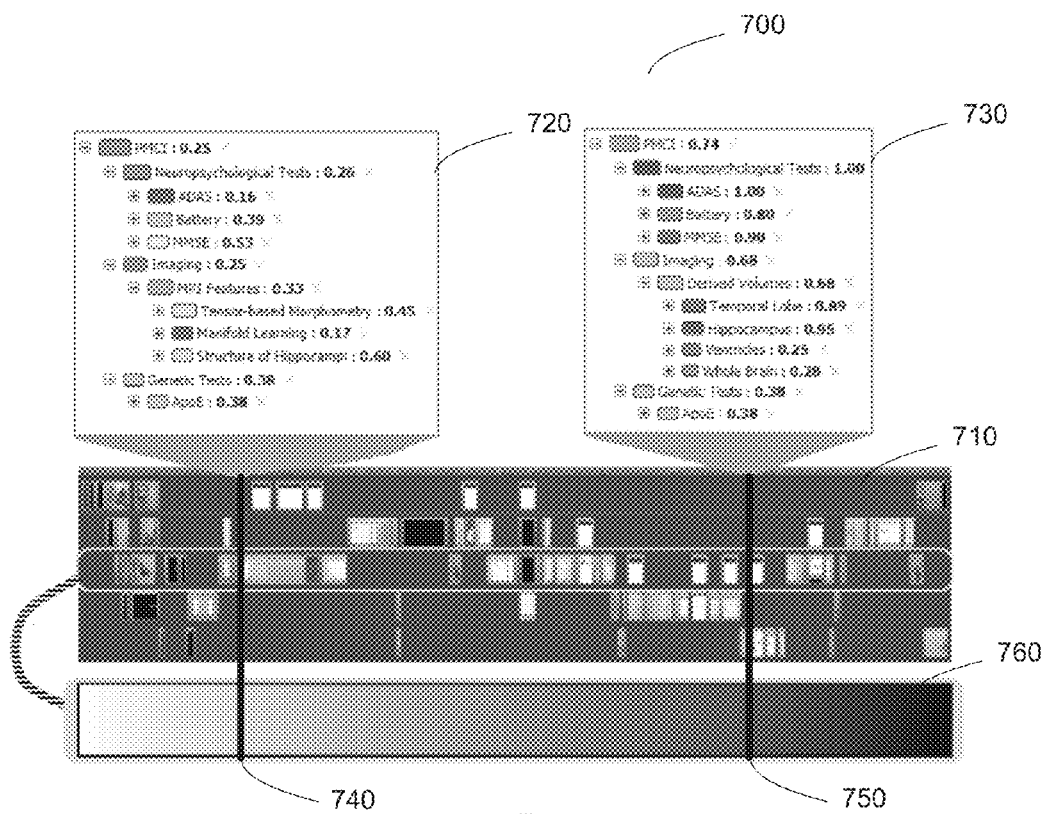
FIG. 7 shows a longitudinal system state analyses view according to an embodiment.
FIG. 8 shows representation and visualization of progress indicator according to an example embodiment.

Longitudinal system state analyses view according to an embodiment of an present disclosure may be visualized with a timeline indicating when data has become available. This is shown in FIG. 7, wherein in the middle is the timeline 710 showing symbolically all available measurements from a patient. From the timeline the user is able to select any time point or any measurement he or she is interested in and see the system state at that time point or the progression of the system state based on the given feature, respectively. Visualization of the system state 720 and 730 at the selected time points 740 and 750 are displayed at the top. Selection can be made to any point in the time. In the bottom, the progression indicator of system state based on the selected indicator is displayed as a bar 760. The progress indicator may be, for example, a progress indicator of MRI features or Alzheimer's Disease Index or any other progress index of measured indicators. The contents of the longitudinal system state analyses 700 may be updated dynamically.

FIG. 8 shows representation and visualization of progress indicator according to an example embodiment. In FIG. 8, the difference value of indicator at given moment (the moment indicated by the location in horizontal direction) is shown by the vertical location of the curve inside the progress indicator bar. To help visual interpretation, the range of possible difference values is shown also by colors using the vertical color gradient. The color codes used are similar to previous figures, i.e., colors are changing, for example, from blue (bottom of bar) to red (top of bar) via white color (middle of bar). If the curve indicating the difference values of the system is on the red area (on the right-top corner in FIG. 8), it would have been shown by a red bean in the visualization of FIG. 5a. Varying measure of goodness values could be represented as shown in FIG. 4d.

Figure 9:
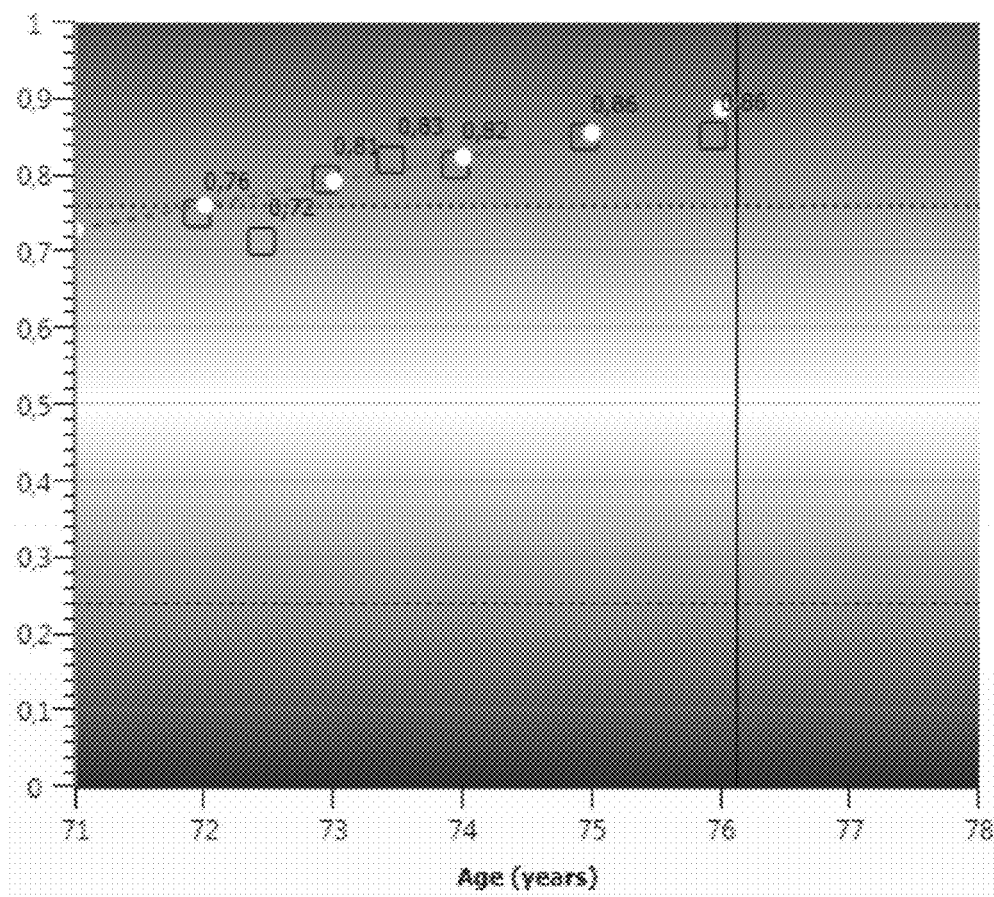
FIG. 9 shows representation and visualization of progress indicator according to an example embodiment.

FIG. 9 shows representation and visualization of progress indicator according to an example embodiment. In FIG. 9, the difference value of indicator at given moment (the moment indicated by the location in horizontal direction) is shown by difference values and also by the vertical location of difference values inside the progress indicator bar. To help visual interpretation, the range of possible difference values is shown also by colors using the vertical color gradient. The color codes used are similar to previous figures, i.e., colors are changing, for example, from blue (bottom of bar) to red (top of bar) via white color (middle of bar).

According to a realization in this present disclosure, indicating the time development of an indicator together with its measure of goodness may provide a good way for making a decision on the state of the system. In other words, seeing the relevant indicators and their time development makes it easier for a user to make a decision, e.g. on whether the person has a brain disease or not.

It is also possible to use difference values for computing trends of the progression between a control and comparison state. The term trend is considered to cover also other functions, such as higher degree polynomials and sigmoid functions, in addition to a line. In FIG. 9, the difference values computed from indicator values obtained at different ages are visualized as blocks, together with a trend line and circles that have been fitted to the indicator values. The trends may be computed with other methods as well. Original difference values in progress indicators may then be replaced with values from the trends, if needed. Current age of a patient in question is shown by a vertical line in the figure.

It needs to be understood that displaying many progress indicators takes up valuable display space. A high number of individual indicators measured at different time points and displayed to a user may be less valuable than seeing the time development of the important indicators. That is, when the measure of goodness is used to modify the progress indicators' size and/or visibility, so that less important indicators take less or no space and the person can concentrate on the important indicators. Thus, displaying the time development of some important indicators may provide more useful information to the user than showing a higher number of different indicators. In other words, removing some indicators from sight, especially those whose measure of goodness is low, may surprisingly be useful when the display space is used for showing the time development of indicators, whose measure of goodness is high.

The various embodiments of the present disclosure can be implemented with the help of computer program code that resides in a memory and causes the relevant apparatuses to carry out the aspects of the present disclosure. For example, a terminal device may comprise circuitry and electronics for handling, receiving and transmitting data, computer program code in a memory, and a processor that, when running the computer program code, causes the terminal device to carry out the features of an embodiment. Yet further, a network device may comprise circuitry and electronics for handling, receiving and transmitting data, computer program code in a memory, and a processor that, when running the computer program code, causes the network device to carry out the features of an embodiment.

It is obvious that the aspects of the present disclosure are not limited solely to the above-presented embodiments, but it can be modified within the scope of the appended claims.

The invention claimed is:

1. A method for determining a state of a system of interest over time using an apparatus comprising a display, wherein the method includes presenting a progress indicator indicative of the state of the system of interest on the display, wherein the apparatus is configured to
    receive biomedical measurement data, wherein said biomedical measurement data relates to at least one indicator of a system of interest and comprises at least two indicator values being indicative of the state of the system of interest and wherein said indicator values are measured at different time points,
    calculate at least one measure of goodness for said indicator by using at least one control state value of said indicator and at least one comparison state value of said indicator, wherein a measure of goodness is configured to indicate, as an index number, an ability of the indicator to differentiate between a control state and a comparison state;
    calculate difference values for said at least two indicator values with reference to the control state and the comparison state, wherein a difference value is configured to indicate a probability of whether the state of the system of interest is closer to the control state or the comparison state, and
    produce a progress indicator for said indicator to determine the state of the system, wherein said progress indicator is presented on the display of the apparatus and presents a change in value of said indicator over time and wherein at least one dimension of said progress indicator is determined on the basis of said at least one measure of goodness so that the progress indicator presented on the display is larger if a value of a measure of goodness is large, and smaller if the measure of goodness is small.

2. A method according to claim 1, wherein the apparatus is further configured to:
    select a part of the progress indicator, and
    view details of the indicator at said part of the progress indicator.

3. A method according to claim 1, wherein said progress indicator is a gradient filled bar, which height and/or length depends on the at least one measure of goodness value for said indicator.

4. A method according to claim 1, wherein said progress indicator comprises beans indicating said difference values, wherein said beans are arranged next to each other and wherein height and/or length of at least one bean depends on the at least one measure of goodness value for said indicator.

5. A method according to claim 3, wherein said progress indicator has at least two different heights or lengths corresponding to different said measure of goodness values and different time instances.

6. A method according to claim 1, wherein said received data relate to at least one further indicator of the system of interest and comprises at least two further indicator values being indicative of the state of the system of interest and wherein said further indicator values are measured at different points in time, wherein the apparatus is further configured to:
    calculate a measure of goodness for said further indicator by using values of said further indicator of at least one control state and at least one comparison state,
    calculate difference values for said at least two further indicator values with reference to said further control and comparison states, and
    define a composite indicator of said indicator and said further indicator,
    calculate a measure of goodness for said composite indicator by using information indicative of said measure of goodness of said indicator and said further indicator,
    calculate difference values for the composite indicator in a system of interest, and
    arranging said composite indicator to be used in inferring the state of the system of interest.

7. A method according to claim 1, wherein the apparatus is further configured to:
    arrange progress bars to be displayed on the basis of the measure of goodness value.

8. An apparatus comprising a processor, non-transitory memory including computer program code, the memory and the computer program code configured to, with the processor, cause the apparatus to:
    receive biomedical measurement data, wherein said biomedical measurement data relates to at least one indicator of a system of interest and comprises at least two indicator values being indicative of the state of the system of interest and wherein said indicator values are measured at different time points,
    calculate at least one measure of goodness for said indicator by using at least one control state value of said indicator and at least one comparison state value of said indicator, wherein a measure of goodness is configured to indicate, as an index number, an ability of the indicator to differentiate between control and comparison states;
    calculate difference values for said measured at least two indicator values with reference to control and comparison states, wherein a difference value is configured to indicate a probability of whether the state of the system of interest is closer to the control state or the comparison state, and produce a progress indicator for said indicator, wherein said progress indicator displays a change in value of said indicator over time and wherein at least one dimension of said progress indicator is determined on the basis of said at least one measure of goodness so that the progress indicator is larger if a value of a measure of goodness is large, and smaller if the value measure of goodness is small.

9. An apparatus according to claim 8, further comprising computer program code configured to, with the processor, cause the apparatus to:

select a part of the progress indicator, and view details of indicator at said part of the progress indicator.

10. An apparatus according to claim 8, wherein said progress indicator is a gradient filled bar, which altitude and/or length depends on the measure of goodness value for said indicator.

11. An apparatus according to claim 8, wherein said progress indicator comprises beans indicating said difference values, wherein said beans are arranged next to each other and wherein altitude and/or length of said beans depend on the measure of goodness value for said indicator.

12. A apparatus according to claim 10, wherein said progress indicator has at least two different heights or lengths corresponding to different said measure of goodness values and different time instances.

13. A system comprising at least one processor, non-transitory memory including computer program code, the memory and the computer program code configured to, with the at least one processor, cause the system to:

receive biomedical measurement data, wherein said biomedical measurement data relates to at least one indicator of a system of interest and comprises at least two indicator values being indicative of the state of the system of interest and wherein said indicator values are measured at different time points, calculate at least one measure of goodness for said indicator by using at least one control state value of said indicator and at least one comparison state value of said indicator, wherein a measure of goodness is configured to indicate, as an index number, an ability of the indicator to differentiate between control and comparison states;

calculate difference values for said measured at least two indicator values with reference to control and comparison states, wherein a difference value is configured to indicate a probability of whether the state of the system of interest is closer to the control state or the comparison state, and produce a progress indicator for said indicator, wherein said progress indicator displays a change in value of said indicator over time and wherein at least one dimension of said progress indicator is determined on the basis of said at least one measure of goodness so that the progress indicator is larger if a value of a measure of goodness is large, and smaller if the value measure of goodness is small.

14. A system according to claim 13, further comprising computer program code configured to, with the processor, cause the system to:

select a part of the progress indicator, and view details of indicator at said part of the progress indicator.

15. A computer program product stored on a non-transient computer readable medium and executable in a data processing device, the computer program product comprising:

a computer program code section for receiving biomedical measurement data, wherein said biomedical measurement data relates to at least one indicator of a system of interest and comprises at least two indicator values being indicative of the state of the system of interest and wherein said indicator values are measured at different time points, calculating at least one measure of goodness for said indicator by using at least one control state value of said indicator and at least one comparison state value of said indicator, wherein a measure of goodness is configured to indicate, as an index number, an ability of the indicator to differentiate between control and comparison states;

calculating difference values for said measured at least two indicator values with reference to control and comparison states, wherein a difference value is configured to indicate a probability of whether the state of the system of interest is closer to the control state or the comparison state, and produce a progress indicator for said indicator, wherein said progress indicator displays a change in value of said indicator over time and wherein at least one dimension of said progress indicator is determined on the basis of said at least one measure of goodness so that the progress indicator is larger if a value of a measure of goodness is large, and smaller if the value measure of goodness is small.

16. A computer program product according to claim 15, further comprising:

a computer program code section for selecting a part of the progress indicator, and a computer program code section for viewing details of indicator at said part of the progress indicator.

17. A computer program product according to claim 15, further comprising: Use of a progress indicator for showing a time development of a biomedical indicator together with a measure of goodness of the indicator.

* * * * *